United States Patent
Wallace et al.

(10) Patent No.: US 7,231,260 B2
(45) Date of Patent: **\*Jun. 12, 2007**

(54) INTRAVASCULAR SELF-ANCHORING ELECTRODE BODY WITH ARCUATE SPRINGS, SPRING LOOPS, OR ARMS

(75) Inventors: Michael P. Wallace, Fremont, CA (US); Robert J. Garabedian, Mountain View, CA (US); Wendelin C. Maners, Hermosa Beach, CA (US); Robert Abrams, Los Gatos, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 336 days.

This patent is subject to a terminal disclaimer.

(21) Appl. No.: 10/841,070

(22) Filed: May 6, 2004

(65) Prior Publication Data

US 2005/0251239 A1  Nov. 10, 2005

(51) Int. Cl.
*A61N 1/00* (2006.01)
(52) U.S. Cl. .................. 607/116; 607/115; 607/129
(58) Field of Classification Search ........ 607/126–128, 607/116, 123; 600/372–374
See application file for complete search history.

(56) References Cited

U.S. PATENT DOCUMENTS

| | | |
|---|---|---|
| 4,141,365 A | 2/1979 | Fischell et al. |
| 4,285,347 A | 8/1981 | Hess |
| 4,519,403 A | 5/1985 | Dickhudt |
| 4,608,985 A | 9/1986 | Crish et al. |
| 4,658,835 A | 4/1987 | Pohndorf |
| 4,739,768 A | 4/1988 | Engelson |

(Continued)

FOREIGN PATENT DOCUMENTS

EP  0 861 676  9/1998

(Continued)

OTHER PUBLICATIONS

IP.com: Electrode Design to Stimulate Blood Vessels, Nerves, or Other Tubular Organs, file://C:\unzipped\IPCOM000010247D1\0_properties.xml, Published Nov. 13, 2002.

(Continued)

*Primary Examiner*—Carl Layno
*Assistant Examiner*—Brian T. Gedeon
(74) *Attorney, Agent, or Firm*—Vista IP Law Group LLP

(57) ABSTRACT

An expandable intravascular medical device comprises an arcuate spring configured to be expanded into contact with the inner surface of a blood vessel. Another medical device comprises an electrode support structure, e.g., a non-tubular arcuate structure or a cylindrical member, and a plurality of resilient spring loops laterally extending from the support structure. The contact created between the loops and a blood vessel is sufficient to anchor the medical device within the blood vessel. In another embodiment, the medical device comprises an elongated member and two resilient spring arms extending distally from the elongated member. The arms are configured to be laterally moved towards each other to place the medical device in a collapsed geometry, and configured to be laterally moved away from each into contact with an inner surface of a blood vessel to place the medical device an expanded geometry.

34 Claims, 11 Drawing Sheets

U.S. PATENT DOCUMENTS

| | | | |
|---|---|---|---|
| 4,813,934 A | 3/1989 | Engelson et al. | |
| 4,869,255 A | 9/1989 | Putz | |
| 4,884,579 A | 12/1989 | Engelson | |
| 5,005,587 A | 4/1991 | Scott | |
| 5,010,894 A | 4/1991 | Edhag | |
| 5,170,802 A | 12/1992 | Mehra | |
| 5,224,491 A | 7/1993 | Mehra | |
| 5,234,437 A | 8/1993 | Sepetka | |
| 5,239,999 A * | 8/1993 | Imran | 600/374 |
| 5,250,071 A | 10/1993 | Palermo | |
| 5,261,916 A | 11/1993 | Engelson | |
| 5,263,488 A | 11/1993 | Van Veen et al. | |
| 5,304,195 A | 4/1994 | Twyford, Jr. et al. | |
| 5,312,415 A | 5/1994 | Palermo | |
| 5,350,397 A | 9/1994 | Palermo et al. | |
| 5,365,926 A | 11/1994 | Desai | |
| 5,391,200 A | 2/1995 | KenKnight et al. | |
| 5,397,341 A * | 3/1995 | Hirschberg et al. | 607/122 |
| 5,411,551 A | 5/1995 | Winston et al. | |
| 5,417,719 A | 5/1995 | Hull et al. | |
| 5,423,864 A | 6/1995 | Ljungstroem | |
| 5,501,703 A | 3/1996 | Holsheimer et al. | |
| 5,509,411 A | 4/1996 | Littmann et al. | |
| 5,531,779 A | 7/1996 | Dahl et al. | |
| 5,534,007 A | 7/1996 | St. Germain et al. | |
| 5,543,864 A | 8/1996 | Hirschman et al. | |
| 5,603,731 A | 2/1997 | Whitney | |
| 5,647,870 A | 7/1997 | Kordis et al. | |
| 5,683,422 A | 11/1997 | Rise | |
| 5,702,438 A * | 12/1997 | Avitall | 607/122 |
| 5,707,354 A | 1/1998 | Salmon et al. | |
| 5,713,922 A | 2/1998 | King | |
| 5,716,377 A | 2/1998 | Rise et al. | |
| 5,752,979 A | 5/1998 | Benabid | |
| 5,782,239 A | 7/1998 | Webster, Jr. | |
| 5,792,187 A | 8/1998 | Adams | |
| 5,800,474 A | 9/1998 | Benabid et al. | |
| 5,814,062 A | 9/1998 | Sepetka et al. | |
| 5,833,709 A | 11/1998 | Rise et al. | |
| 5,846,238 A | 12/1998 | Jackson et al. | |
| 5,860,974 A | 1/1999 | Abele | |
| 5,871,483 A | 2/1999 | Jackson et al. | |
| 5,891,136 A | 4/1999 | McGee et al. | |
| 5,902,236 A | 5/1999 | Iversen | |
| 5,908,385 A | 6/1999 | Chechelski et al. | |
| 5,925,070 A | 7/1999 | King et al. | |
| 5,938,689 A | 8/1999 | Fischell et al. | |
| 5,954,761 A * | 9/1999 | Machek et al. | 607/126 |
| 5,967,986 A | 10/1999 | Cimochowski et al. | |
| 6,015,387 A | 1/2000 | Schwartz et al. | |
| 6,016,449 A | 1/2000 | Fischell et al. | |
| 6,018,682 A | 1/2000 | Rise | |
| 6,027,456 A | 2/2000 | Feler et al. | |
| 6,053,873 A | 4/2000 | Govari et al. | |
| 6,066,163 A | 5/2000 | John | |
| 6,074,407 A | 6/2000 | Levine et al. | |
| 6,074,507 A | 6/2000 | Sukenik | |
| 6,091,980 A | 7/2000 | Squire et al. | |
| 6,094,596 A | 7/2000 | Morgan | |
| 6,119,044 A | 9/2000 | Kuzma | |
| 6,122,548 A | 9/2000 | Starkebaum et al. | |
| 6,128,538 A | 10/2000 | Fischell et al. | |
| 6,136,021 A | 10/2000 | Tockman et al. | |
| 6,141,576 A | 10/2000 | Littmann et al. | |
| 6,161,029 A | 12/2000 | Spreigl et al. | |
| 6,161,047 A | 12/2000 | King et al. | |
| 6,170,488 B1 | 1/2001 | Spillman, Jr. et al. | |
| 6,179,858 B1 | 1/2001 | Squire et al. | |
| 6,205,361 B1 | 3/2001 | Kuzma et al. | |
| 6,216,045 B1 | 4/2001 | Black et al. | |
| 6,231,516 B1 | 5/2001 | Keilman et al. | |
| 6,249,707 B1 | 6/2001 | Kohnen et al. | |
| 6,263,248 B1 | 7/2001 | Farley et al. | |
| 6,266,568 B1 | 7/2001 | Mann et al. | |
| 6,319,251 B1 | 11/2001 | Tu et al. | |
| 6,330,477 B1 | 12/2001 | Casavant | |
| 6,353,762 B1 | 3/2002 | Baudino et al. | |
| 6,360,122 B1 | 3/2002 | Fischell et al. | |
| 6,361,528 B1 | 3/2002 | Wilson et al. | |
| 6,370,427 B1 | 4/2002 | Alt et al. | |
| 6,391,052 B2 | 5/2002 | Buirge et al. | |
| 6,393,325 B1 | 5/2002 | Mann et al. | |
| 6,397,109 B1 | 5/2002 | Cammilli et al. | |
| 6,402,746 B1 | 6/2002 | Whayne et al. | |
| 6,408,214 B1 | 6/2002 | Williams et al. | |
| 6,415,187 B1 | 7/2002 | Kuzma et al. | |
| 6,418,344 B1 | 7/2002 | Rezai et al. | |
| 6,438,427 B1 * | 8/2002 | Rexhausen et al. | 607/126 |
| 6,442,413 B1 | 8/2002 | Silver | |
| 6,442,435 B2 | 8/2002 | King et al. | |
| 6,445,953 B1 | 9/2002 | Bulkes et al. | |
| 6,463,328 B1 | 10/2002 | John | |
| 6,466,822 B1 | 10/2002 | Pless | |
| 6,480,743 B1 | 11/2002 | Kirkpatrick et al. | |
| 6,484,059 B2 | 11/2002 | Gielen | |
| 6,516,227 B1 | 2/2003 | Meadows et al. | |
| 6,519,488 B2 | 2/2003 | KenKnight et al. | |
| 6,522,932 B1 | 2/2003 | Kuzma et al. | |
| 6,529,774 B1 | 3/2003 | Greene | |
| 6,539,263 B1 | 3/2003 | Schiff et al. | |
| 6,547,788 B1 | 4/2003 | Maguire et al. | |
| 6,547,870 B1 | 4/2003 | Griessmann et al. | |
| 6,562,063 B1 | 5/2003 | Euteneuer et al. | |
| 6,584,358 B2 | 6/2003 | Carter et al. | |
| 6,587,733 B1 | 7/2003 | Cross, Jr. et al. | |
| 6,589,230 B2 | 7/2003 | Gia et al. | |
| 6,591,138 B1 | 7/2003 | Fischell et al. | |
| 6,597,953 B2 | 7/2003 | Boling | |
| 6,600,954 B2 | 7/2003 | Cohen et al. | |
| 6,606,521 B2 | 8/2003 | Paspa et al. | |
| 6,647,296 B2 | 11/2003 | Fischell et al. | |
| 6,658,302 B1 | 12/2003 | Kuzma et al. | |
| 6,662,055 B1 | 12/2003 | Prutchi | |
| 6,665,562 B2 | 12/2003 | Gluckman et al. | |
| 6,690,974 B2 | 2/2004 | Archer et al. | |
| 6,697,676 B2 * | 2/2004 | Dahl et al. | 607/126 |
| 6,714,822 B2 * | 3/2004 | King et al. | 607/117 |
| 6,842,648 B2 | 1/2005 | Partridge et al. | |
| 6,895,283 B2 | 5/2005 | Erickson et al. | |
| 6,999,820 B2 * | 2/2006 | Jordan | 607/117 |
| 2001/0025192 A1 | 9/2001 | Gerber et al. | |
| 2001/0041821 A1 | 11/2001 | Wilk | |
| 2001/0053885 A1 | 12/2001 | Gielen et al. | |
| 2002/0111661 A1 | 8/2002 | Cross, Jr. et al. | |
| 2002/0151948 A1 | 10/2002 | King et al. | |
| 2002/0151949 A1 | 10/2002 | Dahl et al. | |
| 2002/0188207 A1 | 12/2002 | Richter | |
| 2003/0014016 A1 | 1/2003 | Purdy | |
| 2003/0040785 A1 | 2/2003 | Maschino et al. | |
| 2003/0199962 A1 | 10/2003 | Struble et al. | |
| 2003/0204135 A1 | 10/2003 | Bystritsky | |
| 2003/0204228 A1 | 10/2003 | Cross, Jr. et al. | |
| 2004/0015193 A1 | 1/2004 | Lamson et al. | |

FOREIGN PATENT DOCUMENTS

| | | |
|---|---|---|
| EP | 0 865 800 A2 | 9/1998 |
| EP | 0 865 800 A3 | 12/1999 |
| EP | 0 864 800 B1 | 9/2004 |
| WO | WO 01/85094 | 11/2001 |

WO    WO 03/077986    9/2003

OTHER PUBLICATIONS

IP.com: Epidural Needle for Spinal Cord Stimulation Electrode, file://C:unzipped\IPCOM000011384D1\0_properties.xml, Published Feb. 14, 2003.

IP.com: Medical Lead System and Method for insertion into the Spinal Cord, file://C:\unzipped\IPCOM000011389D1\0_properties.xml, Published Feb. 17, 2003.

IP.com: Transcutaneous Screening Test for Evaluation of Potential Efficacy of Chronic Trigeminal Neurostimulation as a Therapy for Epilepsy, file://C:\unzipped\IPCOM000011987D1\0_properties.xml, Published Mar. 28, 2003.

IP.com: System and Method for Lead Fixation, file://C:\unzipped\IPCOM000019571D1\0_properties.xml, Published Sep. 19, 2003.

IP.com: Dual Lumen Inflatable Lead, file://C:\unzipped\IPCOM000019703D1\0_properties.xml, Published Sep. 25, 2003.

IP.com: Skull-Mounted Electrical Stimulation System, file://C:\unzipped\IPCOM000019827D1\0_properties.xml, Published Oct. 1, 2003.

IP.com: Spinal Cord Stimulation as a Therapy for Epilepsy, file://C:\unzipped\IPCOM000019881D1\0_properties.xml, Published Oct. 6, 2003.

IP.com: Skull-Mounted Electrical Stimulation System and Method for Treating Patients, file://C:\unzipped\IPCOM000021554D1\0_properties.xml, Published Jan. 22, 2004.

PCT International Search Report for PCT/US2005/010121, Applicant: Boston Scientific Scimed, Inc., Forms PCT/ISA/210 and 220, dated Jul. 4, 2005 (7 pages).

PCT Written Opinion of the International Search Authority for PCT/US2005/010121, Applicant: Boston Scientific Scimed, Inc., Form PCT/ISA/237, dated Jul. 4, 2005 (5 pages).

Canavero, Sergio et al., "Extradural Motor Cortex Stimulation for Advanced Parkinson Disease," J. Neurosurg. 97: pp. 1208-1211, 2002.

Kunieda, Takeharu et al., "Use of Cavernous Sinus EEG in the Detection of Seizure Onset and Spread in Mesial Temporal Lobe Epilepsy," Epilepsia, 41(11): pp. 1411-1419, 2000.

Onal, Cagatay, "Complications of Invasive Subdural Grid Monitoring In Children with Epilepsy," J. Neurosurg. 98: pp. 1017-1026, 2003.

PCT International Search Report for PCT/US2005/006569, Applicant: Boston Scientific Scimed, Inc., Forms PCT/ISA 210 and 220, dated Jun. 13, 2005 (7 pages).

PCT Written Opinion of the International Search Authority for PCT/US2005/006569, Applicant: Boston Scientific Scimed, Inc., Form PCT/ISA/237, dated Jun. 13, 2005 (5 pages).

Web Article: IP.com: "Methods and Placement of Neurostimulation Lead, Infusion Catheter, and/or Sensor Via the Vasculature to the Brain," IPCOM000012135D, Published Apr. 10, 2003 (11 pages).

Web Article: IP.com: "Methods of Placement of Neurostimulation Lead, Infusion Catheter, and/or Sensor Via Peripheral Vasculature." 0349945-003. (7 pages).

* cited by examiner

INTRAVASCULAR SELF-ANCHORING ELECTRODE BODY WITH ARCUATE SPRINGS, SPRING LOOPS, OR ARMS

RELATED APPLICATIONS

This application is related to copending U.S. patent application Ser. No. 10/841,069, filed on the same date, and expressly incorporated herein by reference.

FIELD OF THE INVENTION

The invention relates to the intravascular delivery of medical devices into a patient, and in particular, the intravascular implantation of stimulation and/or recording electrode leads into a patient.

BACKGROUND OF THE INVENTION

There are certain circumstances in which it is desired to electrically stimulate tissue and/or record electrical signals received from such tissue via blood vessels. For example, U.S. patent application Ser. No. 10/744,319, which is expressly incorporated herein by reference, describes a method of treating neurological disorders by intravenously delivering stimulation leads within the brain, thereby obviating the need to invasively create a burr hole in the cranium of the patient.

Despite the minimally invasive benefits provided by these types of procedures, it is preferable that thrombosis formation caused by the blockage of blood flow through a vessel be prevented. It is also preferable that the electrical energy delivered by the vessel implanted electrode lead be as efficient as possible. For example, when treating a neurological disorder using electrical energy, it is desirable that the magnitude of the electrical energy be sufficient to cause sub-threshold stimulation of the targeted brain tissue. Due to the relatively low resistance of blood versus the relatively high resistance of vessel walls, however, the electrical energy is likely to follow the path of least resistance, i.e., through the blood stream, rather than the vessel wall. The gain of the implanted stimulation device could be increased in order to overcome the power losses through the bloodstream. Invariably, this may potentially cause poor sub-threshold stimulation of the target area, or worse, stimulation of a non-targeted region of the brain. Increasing the gain can also impact the system efficiency by reducing the battery life of the implanted stimulation source.

Thus, there remains a need to provide improved intravascular electrode leads that are capable of more efficiently transmitting electrical energy into vessel tissue and receiving electrical energy from vessel tissue, while minimizing the occlusion of blood flow.

SUMMARY OF THE INVENTION

In accordance with a first aspect of the present inventions, another expandable intravascular medical device is provided. The medical device comprises an electrode support structure, e.g., a non-tubular arcuate structure or a cylindrical member. The medical device further comprises at least one electrode associated with the support structure. For example, the electrode(s) can be discrete elements that are bonded to the support structure, electrically conductive layers disposed on the support structure, or the support structure, itself, can form the electrode(s). The medical device further comprises a plurality of resilient spring loops laterally extending from the support structure. The electrode(s) may optionally be formed from the spring loops. The medical device further comprises at least one lead electrically coupled to the electrode(s). Alternatively, if there are a plurality of electrodes, a plurality of leads can be electrically coupled to the respective electrodes.

In accordance with a second aspect of the present inventions, a method of performing a medical procedure on a patient is provided. The method comprises intravascularly introducing the afore-mentioned medical device into the patient while the medical device is in a collapsed geometry (e.g., by applying a compressive force to the spring loops), placing the medical device in an expanded geometry (e.g., by releasing the compressive force from the spring loops) to firmly contact the electrode(s) with the inner surface of a blood vessel, and transmitting and/or receiving electrical signals between the blood vessel and the electrode(s). In one preferred method, the medical device is implanted within the blood vessel.

Thus, although the present inventions should not be so limited in their broadest aspects, the firm placement of the electrode(s) against the inner surface of the vessel wall by the action of the spring loops allows the electrical energy to be more efficiently transmitted to and/or received from the vessel wall and surrounding tissue, while minimizing the occlusion of blood flow. In addition, due to their placement on one side of the vessel wall, the electrode(s) focus the transmission of the electrical energy into and/or the reception of the electrical energy from a targeted tissue site.

In accordance with a third aspect of the present inventions, an intravascular medical device is provided. The medical device comprises an elongated member and two resilient spring arms extending distally from the elongated member. The arms are configured to be laterally moved towards each other to place the medical device in a collapsed geometry, and configured to be laterally moved away from each into contact with an inner surface of a blood vessel to place the medical device an expanded geometry.

In one embodiment, the spring arms are pre-shaped to laterally move away from each other. The contact created between the respective arms and the blood vessel are sufficient to anchor the medical device within the blood vessel. The medical device further comprises an electrode associated with the distal end of one of the spring arms. For example, the electrode can be a discrete element that is bonded to the spring arm, an electrically conductive layer disposed on the spring arm, or the distal end of the arcuate spring, itself, can form the electrode. The medical device may comprise another electrode associated with the distal end of the other of the spring arms. The medical device further comprises a lead electrically coupled to the electrode. Alternatively, if there are two electrodes, a two leads can be electrically coupled to the respective electrodes.

In accordance with a fourth aspect of the present inventions, a method of performing a medical procedure on a patient is provided. The method comprises intravascularly introducing the afore-mentioned medical device into the patient while the medical device is in a collapsed geometry (e.g., by applying a compressive force to the spring arms), placing the medical device in an expanded geometry (e.g., by releasing the compressive force from the spring arms) to firmly contact the electrode with the inner surface of a blood vessel, and transmitting and/or receiving electrical signals between the blood vessel and the electrode. In one preferred method, the medical device is implanted within the blood vessel.

Thus, although the present inventions should not be so limited in its broadest aspects, the firm placement of the electrode(s) against the inner surface of the vessel wall by the action of the spring arms allows the electrical energy to be more efficiently transmitted to and/or received from the vessel wall and surrounding tissue, while minimizing the occlusion of blood flow.

In accordance with a fifth aspect of the present inventions, an expandable intravascular medical device is provided. The medical device comprises an arcuate spring configured to be expanded into firm contact with the inner surface of a blood vessel. The arcuate spring is non-tubular, i.e., it spans less than 360 degrees. In one embodiment, the arcuate spring spans greater than 180 degree. This allows the arcuate spring to more easily anchor the medical device to the inner surface of a blood vessel when expanded.

The medical device further comprises at least one electrode associated with the arcuate spring. For example, the electrode(s) can be discrete elements that are bonded to the arcuate spring, electrically conductive layers disposed on the arcuate spring, or the arcuate spring, itself, can form the electrode(s). The medical device further comprises at least one lead electrically coupled to the electrode(s). Alternatively, if there are a plurality of electrodes, a plurality of leads can be electrically coupled to the respective electrodes.

In accordance with a sixth aspect of the present inventions, a method of performing a medical procedure on a patient is provided. The method comprises intravascularly introducing the afore-mentioned medical device into the patient while the medical device is in a collapsed geometry (e.g., by applying a compressive force to the arcuate spring), placing the medical device in an expanded geometry (e.g., by releasing the compressive force from the arcuate spring) to firmly contact the electrode(s) with the inner surface of a blood vessel, and transmitting and/or receiving electrical signals between the blood vessel and the electrode(s).

Thus, although the present inventions should not be so limited in their broadest aspects, the firm placement of the electrode(s) against the inner surface of the vessel wall by the action of the arcuate spring allows the electrical energy to be more efficiently transmitted to and/or received from the vessel wall and surrounding tissue, while minimizing the occlusion of blood flow. Also, the non-tubular nature of the arcuate spring allows the medical device to adapt to various sizes of blood vessels as compared to tubular structures. In addition, due to the non-tubular nature of the arcuate spring, the electrode(s) can be more easily configured to focus the transmission of the electrical energy into and/or the reception of the electrical energy from a targeted tissue site.

In accordance with an eighth aspect of the present inventions, still another intravascular medical device is provided. The medical device comprises an arcuate structure with an inner electrically insulative surface. The arcuate structure may either be tubular or non-tubular. The medical device further comprises at least one electrode associated with the arcuate structure. In one embodiment, at least a portion of the arcuate structure forms the electrode(s). In another embodiment, the arcuate structure has an outer insulative surface, and the electrode(s) are disposed on the arcuate structure as a thin electrically conductive film. In either case, if the arcuate structure is resilient, the electrode(s) will be able to flex with the arcuate structure. In another embodiment, the arcuate structure is non-porous to enhance the electrical insulative nature of the arcuate structure. The medical device further comprises at least one lead electrically coupled to the electrode(s). Alternatively, if there are a plurality of electrodes, a plurality of leads can be electrically coupled to the respective electrodes.

In accordance with a ninth aspect of the present inventions, a method of performing a medical procedure on a patient is provided. The method comprises intravascularly introducing the afore-mentioned medical device into the patient while the medical device is in a collapsed geometry (e.g., by applying a compressive force to the arcuate structure), placing the medical device in an expanded geometry (e.g., by releasing the compressive force from the arcuate structure) to firmly contact the electrode(s) with the inner surface of a blood vessel, and transmitting and/or receiving electrical signals between the blood vessel and the electrode(s). In one preferred method, the medical device is implanted within the blood vessel.

Thus, although the present inventions should not be so limited in its broadest aspects, the existence of the inner insulative surface of the arcuate structure electrically insulates the blood from electrical energy transmitted and/or received by the electrode(s), while minimizing the occlusion of blood flow.

BRIEF DESCRIPTION OF THE DRAWINGS

The drawings illustrate the design and utility of preferred embodiment(s) of the invention, in which similar elements are referred to by common reference numerals. In order to better appreciate the advantages and objects of the invention, reference should be made to the accompanying drawings that illustrate the preferred embodiment(s). The drawings, however, depict the embodiment(s) of the invention, and should not be taken as limiting its scope. With this caveat, the embodiment(s) of the invention will be described and explained with additional specificity and detail through the use of the accompanying drawings in which.

DETAILED DESCRIPTION OF THE PREFERRED EMBODIMENTS

Figure 1:
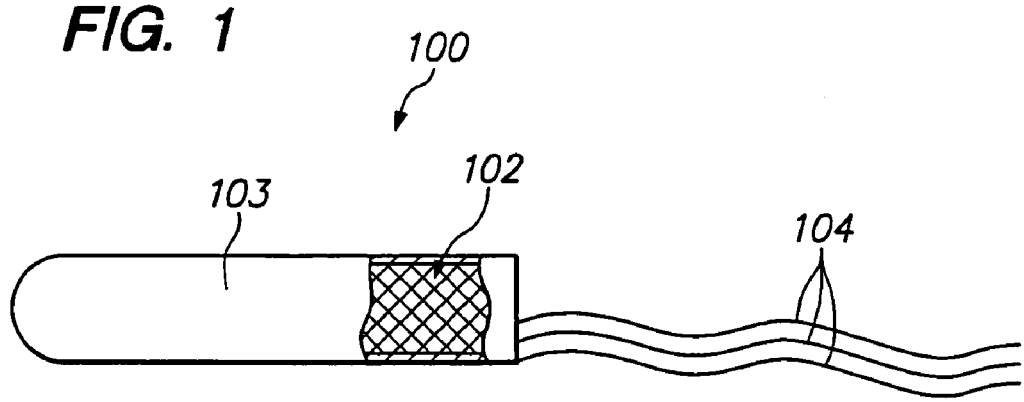
FIG. 1 is a partially cutaway side view of an intravascular medical device constructed in accordance with a preferred embodiment of the present inventions, wherein the medical device is particularly shown in a collapsed geometry.
Figure 2:
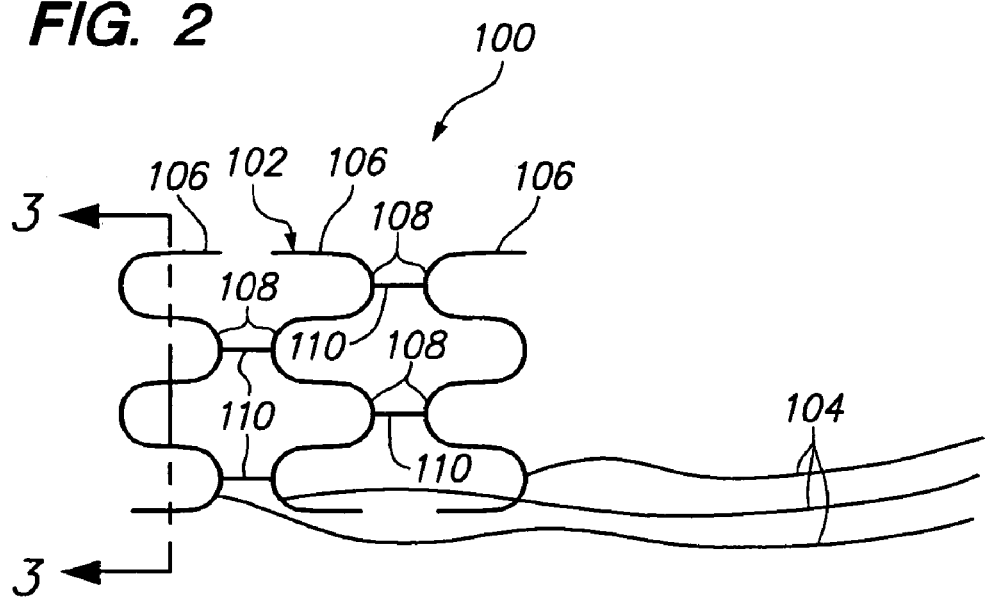
FIG. 2 is a side view of the medical device of FIG. 1, particularly shown in an expanded geometry.
Figure 3:
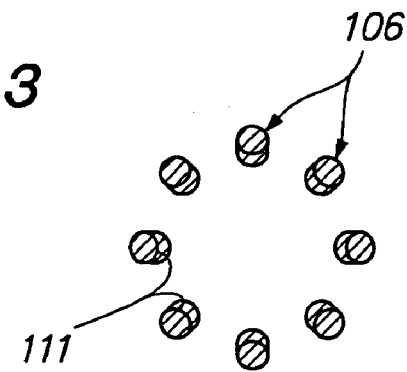
FIG. 3 is a cross-sectional view of the medical device of FIG. 2, taken along the line 3—3.

Referring now to FIGS. 1–3, an intravascular medical device 100 constructed in accordance with a preferred embodiment of the present inventions will be described. The medical device 100 comprises an expandable/collapsible tubular electrode body 102, and a plurality of flexible conductive leads 104 electrically coupled to the electrode body 102. For the tubular body can either be continuous tubular structure or a structure that has a tubular profile, such as a coil. The electrode body 102 can be transformed from a collapsed geometry (FIG. 1) into an expanded geometry (FIG. 2). In its collapsed geometry, the medical device 100 can be intravascularly delivered to a target site within a vessel using a standard stent delivery apparatus. In order to maintain the medical device 100 in its collapsed geometry, a removable sheath or covering 103 is disposed over the collapsed electrode body 102. The sheath 103 may have one or more delivery wires (not shown) that can be pulled in order to remove the sheath 103 from the electrode body 102, thereby allowing the medical device 100 to be placed in its expanded geometry.

When the medical device 100 is in its expanded geometry, the electrode body 102 can be placed into firm contact with the target site and used to transmit to and/or receive electrical signals from the blood vessel and surrounding tissue, while minimizing blood occlusion. The leads 104, the proximal ends of which will extend from the intravascular access point in the patient (e.g., the femoral vein or jugular vein), are configured to be coupled to an implanted or external source and/or recorder of the electrical signals (not shown), as will be described in further detail below.

The electrode body 102 comprises a plurality of electrically conductive sub-structures 106 (in this case, three), which together, form an integrated support structure. In the preferred embodiment, the conductive sub-structures 106 are self-expanding (i.e., they automatically expand in the absence of a radially compressive force). Alternatively, the conductive sub-structures 106 expand only in the presence of a radially expanding force, such with a stent balloon (not shown). In any event, once expanded, the rigidity of the conductive sub-structures 106 will allow them to remain in their expanded geometry until a radially compressive force is applied.

Figure 4:
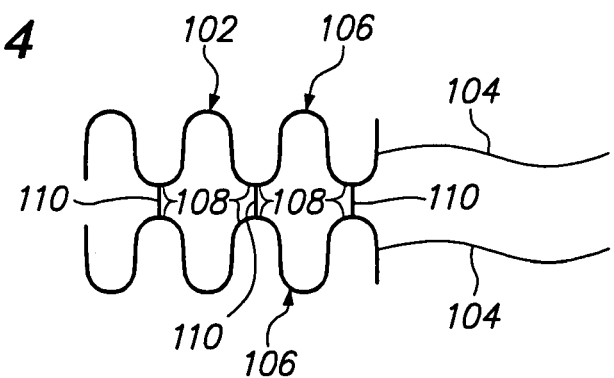
FIG. 4 is a side view of a modification of the medical device of FIG. 2, particularly shown in an expanded geometry.

In the preferred embodiment, the conductive sub-structures 106 are distinct in that they are separately formed, and then they are linked together to form the integrated structure. In the illustrated embodiment, the conductive sub-structures 106 are cylindrical structures that are axially aligned along the length of the electrode body 102. In this case, the conductive sub-structures 106 act as three ring electrodes that extend along the electrode body 102. Alternatively, as illustrated in FIG. 4, each conductive support structure 106 takes the form of semi-cylindrical structure that extends partially around the electrode body 102. In this case, two semi-circular conductive sub-structures 106 are linked together along the axis of the electrode body 102 to form an upper electrode and a lower electrode. In alternative embodiments, the semi-cylindrical conductive sub-structures 106 can be further divided to create additional electrodes.

In any event, each conductive sub-structure 106 is skeletal in nature, and is formed by fashioning a wire or wires into an undulating shape, as illustrated in FIGS. 2 and 4. Alternatively, the wire or wires can be fashioned into a mesh, braid, or coil to form the skeletal structure. Alternatively, each conductive sub-structure 106 may not be skeletal in nature, but rather may be composed of a resilient continuous material. The diameter of the wire used to make each conductive sub-structure 106 preferably has a diameter to provide a hoop strength to the conductive sub-structure 106 sufficient to hold the electrode body 102 in place within the selected blood vessel without moving as a result of the repetitive blood pulsing within the vascular system, but without distending the vessel wall.

In whichever manner fashioned, the material used to form each conductive sub-structure 106 is both biocompatible and electrically conductive. Preferably, such material is also radiopaque and allows for electrolytic detachable linkages to the proximal end of the electrode body 102, as will be described in further detail below. Suitable metals and alloys for the composition of the support structure include Platinum Group metals, especially platinum, rhodium, palladium, rhenium, as well as tungsten, gold, silver, tantalum, and alloys of these metals, such as a platinum/tungsten alloy. Each conductive sub-structure 106 can also be composed of a wide variety of stainless steels if some sacrifice of radiopacity can be tolerated. Certain super-elastic alloys, such as nickel/titanium alloys, nickel/titanium alloys, or nickel/aluminum alloys, can also be used. Especially preferred is the titanium/nickel alloy known as "nitinol," which is a very sturdy alloy that will tolerate significant flexing. If desired, the wire used to form the conductive sub-structure 106 can be further coated with platinum-iridium, gold, or silver to improve its conduction properties, biocompatibility, and radiopacity. Each conductive sub-structure 106 can be coated with additives, such as a non-thrombogenic agent to prevent blood coating, or a therapeutic agent.

Figure 5:
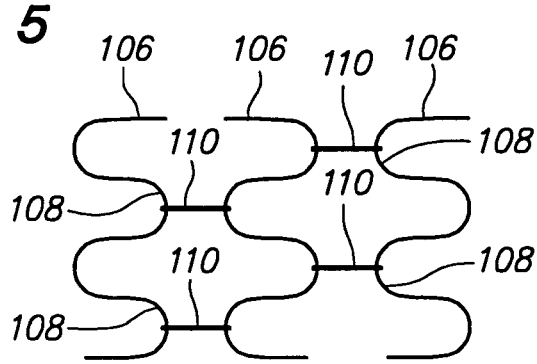
FIG. 5 is a close-up view of the medical device of FIG. 2.
Figure 6:
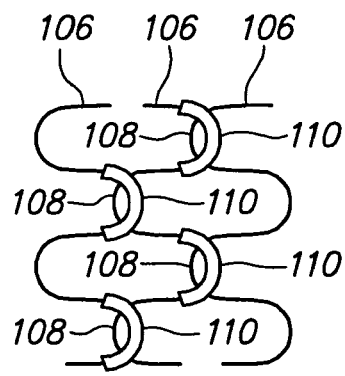
FIG. 6 is a close-up view of another modification of the medical device of FIG. 2, particularly shown in an expanded geometry

The portions of the conductive sub-structures 106 that are mechanically linked together (i.e., the loops 108 at the edges of the conductive sub-structures 106) are electrically isolated from each other. In the embodiments illustrated in FIGS. 2 and 4, a plurality of electrically insulative elements 110 are connected between the loops 108, thereby mechanically linking, while electrically isolating, the conductive sub-structures 106, as illustrated in FIG. 5. Although the insulative elements 110 are shown in FIGS. 2, 4, and 6 as single strands of material, the insulative elements 110 can have other shapes and forms, e.g., a loop or a hook. The insulative elements 110 can be composed of a suitably biocompatible and non-conductive material, such as silicone, nylon, Pebax®, polyimide, or urethane. The insulative elements 110 can be discrete elements that are bonded to the loops 108 of the respective conductive sub-structures 106 using a suitable material, such as silicone, Pebax®, and urethane, or can be formed by, e.g., microinjecting a non-conductive material, such as silicone, Pebax®, or urethane, between the loops 108. Preferably, the insulative elements 100 have sufficient axial rigidity to maintain the spatial separation between the sub-structures 106 to avoid electrical shorting.

Figure 28:
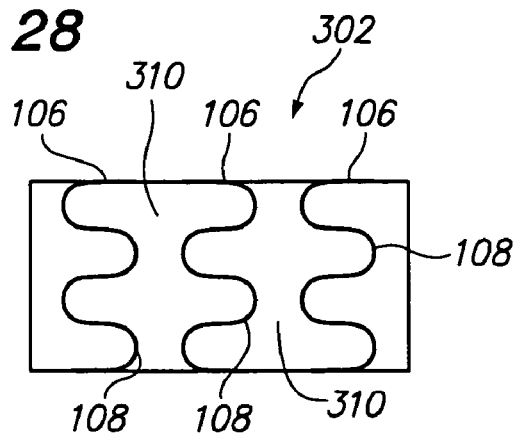
FIG. 28 is a side view of another modification of the medical device of FIG. 2, particularly shown in an expanded geometry.

Although each insulative element 110 is shown as only connecting a pair of loops 108 together, an insulative element 110 can connect a series of loop pairs. For example, FIG. 28 illustrates an alternative electrode body 302 that electrically isolates the conductive sub-structures 106 with insulative tubular elements 310 that circumferentially extend around the electrode body 302. The tubular elements 310 can be integrated into a single tubular member, in which case, the conductive sub-structure 106 can be bonded to the exterior surface of the tubular member, or may be embedded into the tubular member. Alternatively, the tubular elements 310 may be formed between the respective conductive sub-structures 106 as discrete pieces, e.g., by injection molding insulative material between the sub-structures 106.

Figure 29:
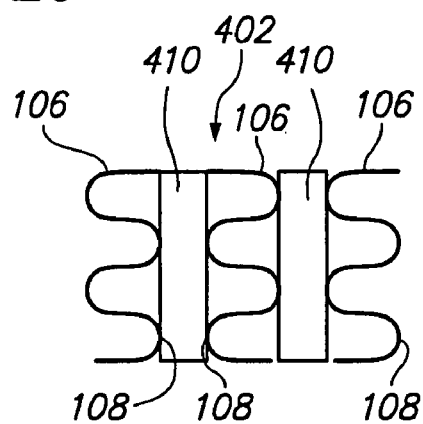
FIG. 29 is a side view of still another modification of the medical device of FIG. 2, particularly shown in an expanded geometry.

In the embodiment illustrated in FIG. 28, the tubular elements 310 are in contact with every portion of the conductive sub-structures 106. Alternatively, as illustrated in FIG. 29, another electrode body 402 comprises tubular elements 410 that are only formed between the loops 108 of the respective sub-structures 106. In this case, the substructures 106 can be bonded to the tips of the loops 108 using suitable means, such as an adhesive or melting, or the tubular elements 410 can be micro-injected between the loops 108. It should be noted that the tubular elements 310 and 410 illustrated in FIGS. 28 and 29 primarily exist to provide electrical insulation to the sub-structures 106, and do not significantly affect the radial spring force provided by the conductive sub-structures 106.

Figure 30:
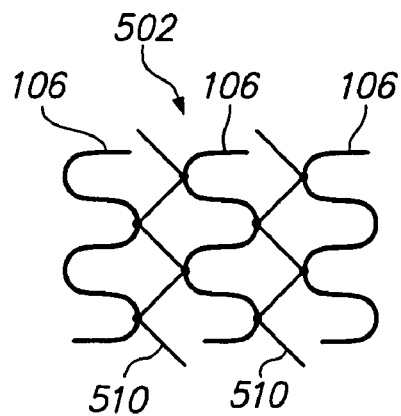
FIG. 30 is a side view of yet another modification of the medical device of FIG. 2, particularly shown in an expanded geometry.

FIG. 30 illustrates an alternative electrode body 502 that electrically isolates the conductive sub-structures 106 with a plurality of insulative elements 510 that connect the loops 108 of a pair of conductive sub-structures 106 in a zig-zag shape. The zig-zagged insulative elements 510 can be made by, e.g., bonding or embedding the conductive sub-structures 106 onto or into an electrically insulative tubular member, similar to that shown in FIG. 28, and then etching away the insulative material to form the insulative elements 510.

In an alternative embodiment illustrated in FIG. 6, the loops 108 of the conductive sub-structures 106 are directly linked together. In this case, insulative elements 110 take the form of an insulative coating applied to one loop 108 of each connected loop pair, thereby electrically insulating the directly linked conductive sub-structures 106 from each other. It should be noted that directly linking the conductive sub-structures 106 in this manner facilitates the retrievability of the electrode body 102. That is, since the loops 108 are tightly fitted together, snagging of the loops 108 as the electrode body 102 is pulled into a sheath is minimized.

As illustrated in FIG. 3, the electrode body 102 can optionally have a layer of insulative material 111, such as elastic or silicone, disposed on the inner surface of the conductive sub-structures 106. In this manner, if the electrode body 102 is used to convey stimulation energy, or otherwise transmit electrical signals, radially inward transmission of the electrical energy or signals through the blood is prevented, thereby efficiently focusing it radially outward into the vessel wall and surrounding tissue where it is needed.

In whichever manner the conductive sub-structures 106 are linked and electrically isolated, the leads 104 are connected to the electrode body 102 using suitable means, such as welding or soldering. Each lead 104 comprises an electrically conductive core with an outer insulative layer. The length of the lead 104 is preferably sized to extend from intravascular access point in the patient to the selected target site within the blood vessel where the electrode body 102 will be implanted. If the medical device 100 is to be connected to the implanted stimulator or recorder, the length of the lead 104 should be sized to extend from the implantation site of the stimulator and/or recorder to the selected target site when routed through the intravascular access point. For example, if the target site is in the patient's brain, the implantation site of the stimulator or recorder is in the chest region of the patient, and the intravascular access point is the patient's jugular vein, then the length of the lead 104 may be in the range of 50 cm to 100 cm. If, however, the target site is in the patient's brain, the implantation site of the source or recorder is in the abdominal region of the patient, and the intravascular access point is the patient's femoral vein, then the length of the lead 104 may be in the range of 150 cm to 300 cm.

The leads 104 can be coupled to the electrode body 102 in a variety of manners to achieve different electrode functionalities. For example, in the illustrated embodiment, the leads 104 are coupled to the respective conductive sub-structures 106, so that the conductive sub-structures 106 are completely electrically isolated from one another. In this manner, the electrode body 102 can have a multiple-channel and/or multi-polar capability. That is, if operating as a multi-channel device, the conductive sub-structures 106 can simultaneously receive multiple signals (if connected to a recorder) or can simultaneously transmit multiple signals (if connected to a stimulation source). If operated as a multi-polar device, electrical signals can be transmitted between one or more conductive sub-structures 106 (as anodes) and one or more other conductive sub-structures (as cathodes). Of course, the conductive sub-structures 106 can be electrically combined to make a single-channel and/or monopolar device if the proximal ends of the leads 104 are electrically connected together at the stimulator and/or recorder. In an alternative embodiment, a single lead 104 can be coupled to one of the conductive sub-structures 106, preferably the proximal-most conductive sub-structure 106, in which case, the conductive sub-structures 106 can be electrically coupled together in series, e.g., by directly or indirectly electrically coupling a pair of respective loops 108 together.

It should be noted that electrode body 102 may alternatively have a wireless transmitter and/or receiver in order to provide the electrode body 102 with the capability of wirelessly communicating with a remote stimulator and/or recorder. In this case, the leads will be routed from the electrodes on the electrode body 102 to the transmitter and/or receiver.

Figure 7:
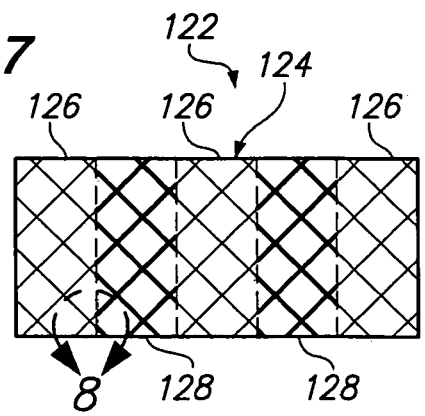
FIG. 7 is a side view of another alternative embodiment of the medical device of FIG. 2.

Although the previously described electrode body 102 has been described as having discrete conductive sub-structures, the electrode body 102 can be formed from a unibody support structure. In particular, FIG. 7 illustrates an electrode body 122 that forms cylindrically-shaped electrically conductive regions 126 (delineated by the dashed line) extending around the electrode body 122, and electrically insulative regions 128 extending around the electrode body 102 between the conductive regions 126.

Figure 8:
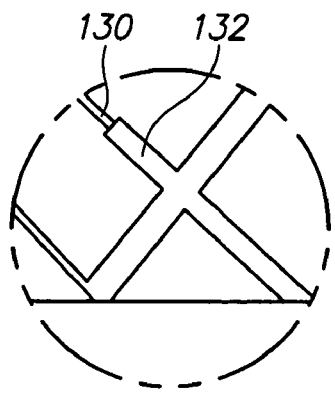
FIG. 8 is a close-up view of the medical device of FIG. 7, taken along the lines 8—8.

Like the previously described conductive sub-structures 106, the unibody support structure 124 is skeletal in nature and, in this case, is formed as a tubular mesh. The wires used to form the unibody support structure 124, however, comprises an electrically conductive core 130 and an insulative layer 132 disposed over the conductive core 130, as best shown in FIG. 8. The conductive regions 126 are formed by removing the insulative layer 132 from portions of the support structure 124 (in this case, cylindrical portions) in order to expose the underlying conductive core 130. Removal of the insulative layer 132 can be accomplished in any suitable manner, including mechanical, chemical, or laser etching. Thus, the exposed portions of the support structure 124 serve as the conductive regions 128, and the unexposed portions of the support structure 124 serve as the insulative regions 128. The electrically conductive leads 104 can be coupled to the electrode body 102 in the same manner described above, with the exception that the leads 104 are coupled to the conductive core 130 of the support structure 132.

Figure 9:
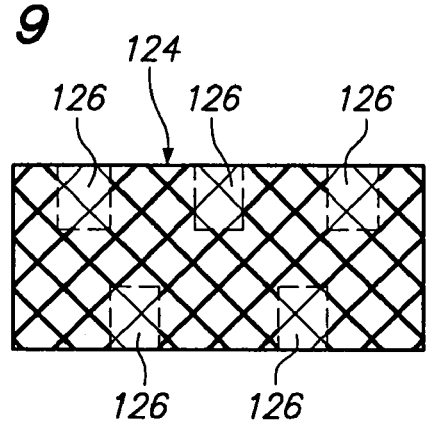
FIG. 9 is a side view of a modification of the medical device of FIG. 7.

The conductive and insulative regions 126/128 of the electrode body 102 can be formed into other shapes besides cylindrical shapes. For example, as illustrated in FIG. 9, the conductive regions 126 are formed as rectangular patches that are disposed about the electrode body 102. Thus, it can be appreciated that forming the electrode body 122 out of a unibody support structure in this manner provides great flexibility in providing various shapes and configurations of electrodes onto the body 122.

Figure 10:
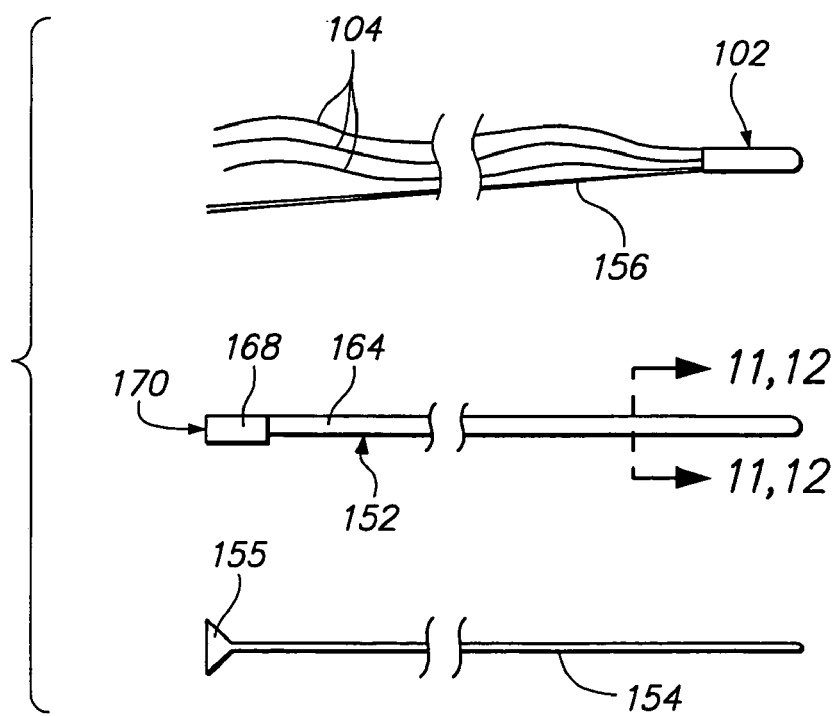
FIG. 10 is a plan view of an intravascular delivery kit used to deliver the medical device of FIG. 1 into a patient.

Referring now to FIG. 10, an intravascular lead kit 150 arranged in accordance with one preferred embodiment of the present invention is illustrated. The kit 150 comprises the previously described medical device 100, a delivery catheter 152 configured for intravascularly delivering the medical device 100 into selected blood vessels within the patient's body, a guidewire 154 configured for guiding the delivery catheter 152 into the selected blood vessels, and a detachable pusher element 156 configured for deploying the medical device 100 from the delivery catheter 152 into a selected region within a blood vessel.

The pusher element 156 is mechanically coupled to the electrode body 102, and is axially rigid, so that the electrode body 102 can be introduced through the catheter 152, yet laterally flexible to allow the pusher element 156 to bend around the natural curves within the patient's vasculature. In the illustrated embodiment, the pusher element 156 can be selectively detached from the electrode body 102 (once properly placed) using an electrolytic arrangement.

Figure 13:
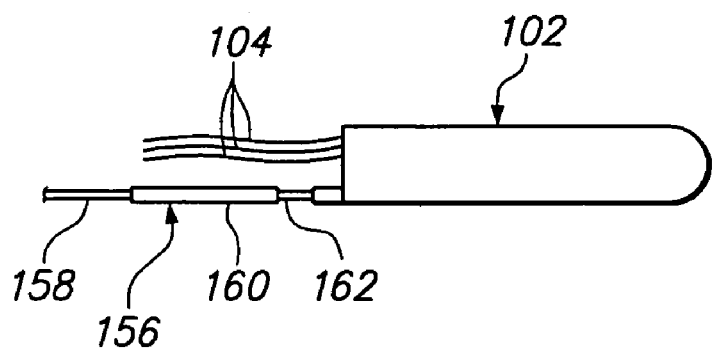
FIG. 13 is a close-up side view of the electrode body of the medical device of FIG. 1, particularly showing the attachment of an electrolytic pusher wire used in the delivery kit of FIG. 10.

In particular, as illustrated in FIG. 13, the pusher element 156 comprises an electrically conductive core wire 158 composed of a material that will electrolytically dissolve in an aqueous fluid medium, such as blood, saline solution, or other bodily fluid. Materials that are capable of electrolytically dissolving are steel, stainless steel, nickel, and nickel/titanium alloys. The electrode body 102 may be suitably coupled to the distal end of the core wire 158 using means, such as crimping, soldering, or welding. The pusher element 156 further comprises an insulative sleeve 160 that, with the exception of a small sacrificial portion 162 just proximal to the mounted electrode body 102, covers the core wire 158. The length of the sacrificial portion 162 is preferably small. For instance, it may be as short as 0.010 inches, and typically no longer than 0.150 inches in length. The insulative sleeve 160 is composed of a material that will not decompose prior to the sacrificial portion 162 of the core wire 158. For example, the insulative sleeve 160 may be composed of polytetrafluoroethylene, fluoropolymers, polyurethane, parylene, polyethylene, polypropylene, polyethylene terephthalate, or other known suitable, typically polymeric, material. Thus, it can be appreciated that when electrical current is delivered through the core wire 158, while the distal end of the pusher element 156 is exposed to blood, the sacrificial portion 162 of the core wire 158 will disintegrate, thereby releasing the electrode body 102. Additional details regarding the use of pusher wires with electrolytic detachment means are disclosed in U.S. Pat. No. 6,589,230, which is expressly incorporated herein by reference.

In alternative embodiments, pusher wires with mechanical detachment mechanisms can be used to selectively detach the electrode body 102. For example, U.S. Pat. Nos. 5,234,437, 5,250,071, 5,261,916, 5,304,195, 5,312,415, and 5,350,397, which are expressly incorporated herein by reference, disclose such mechanically detachable means.

Figure 11:
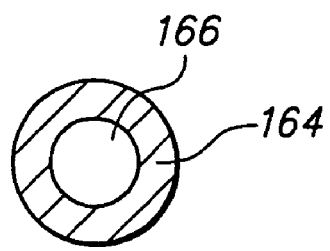
FIG. 11 is a cross-sectional view of a delivery catheter used in the delivery kit of FIG. 10, taken along the line 11—11.

The delivery catheter 152 comprises an elongate, flexible, catheter body 164, and a delivery lumen 166 (shown in FIG. 11) extending the length of the catheter body 164. The delivery lumen 166 is sized to alternately receive a guidewire 154 and the medical device 100. The delivery catheter 152 further comprises a proximal adapter 168 suitably mounted on the proximal end of the catheter body 164. The proximal adapter 168 comprises a port 170 out which the guidewire 154 and medical device 100. Alternatively, dedicated guidewire and electrode lead lumens, along with respective ports, can be provided.

The catheter body 164 is composed of a medically acceptable material, preferably a nondistensible polymer having the appropriate mechanical properties. Preferred materials include polyethylene, polyester, polypropylene, polyimide, polyvinyl chloride, ethylvinyl acetate, polyethylene terephthalate, polyurethane, Pebax®, fluoropolymers, silicone, and their mixtures and block or random copolymers. The catheter body 164 preferably has a relatively stiff proximal segment, which makes up between 70%–95% of the total length of the catheter body 164, and a relatively flexible distal segment, which makes up the remaining 5%–30% of the length of the catheter body 164.

Figure 12:
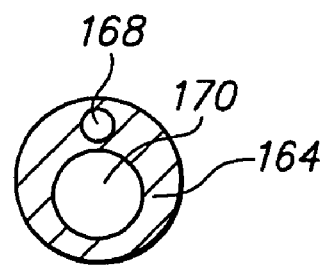
FIG. 12 is a cross-sectional view of another delivery catheter used in the delivery kit of FIG. 10, taken along the line 12—12.

The delivery lumen 166 of the catheter 152 preferably has a diameter of between 2–50 mils, but ultimately will be sized to allow the guidewire 154 and medical device 100 to be respectively introduced therethrough. Alternatively, as shown in FIG. 12, the catheter 152 may comprises separate lumens 168 and 170 for respectively receiving the guidewire 154 and medical device 100. The outer diameter of the catheter body 164 is preferably between 8–80 mils, but ultimately will be sized such that blood flow is not occluded within the smallest blood vessel through which the delivery catheter 152 will be introduced. For example, the vessel site may be within a small diameter vessel having a 2–5 mm diameter and accessible by way of a tortuous vessel path, which may involve sharp vessel turns and multiple vessel branches. In this case, the catheter 152 preferably has a small, flexible construction with a diameter of less than 40 mil, and preferably between 8–30 mils. The length of the catheter body 164 will typically be from 50–300 cm, depending on the total linear length of the blood vessels that the delivery catheter 152 must traverse from its entry point into the patient's vasculature to the target delivery site of the electrode body 102.

Referring back to FIG. 10, the guidewire 154 may have any suitable construction for guiding the delivery catheter 152 to its intended site in the brain. Typically, the length of the guidewire 154 is at least about 10–50 cm longer than the length of the catheter 152, such that the distal end of the guidewire 154 can be extended several centimeters or more beyond the distal end of the delivery catheter 152, while allowing the proximal end of the guidewire 154 to be manipulated, such as by torqueing. The proximal end of the guidewire 154 is equipped with a handle 155 for applying torque to the wire during catheter operation. The guidewire 154 may optionally include radiopaque bands (not shown) for visualization under fluoroscopy. Additional details regarding the structure and dimensions of guidewires suitable for guiding catheters into the vasculature of the brain are disclosed in U.S. Pat. No. 6,074,507, which is expressly incorporated herein by reference.

It should be noted that the kit illustrated in FIG. 10 is not the only manner in which the medical device 100 can be delivered to a vessel target site, but rather there are other means of delivering the medical device 100 into a vessel. For example, the medical device 100 can be delivered within a vessel by mounting the electrode body 102 around the distal end of a catheter, as disclosed in U.S. Pat. Nos. 5,534,007 and 6,562,063, which are expressly incorporated herein by reference.

Figure 14A:
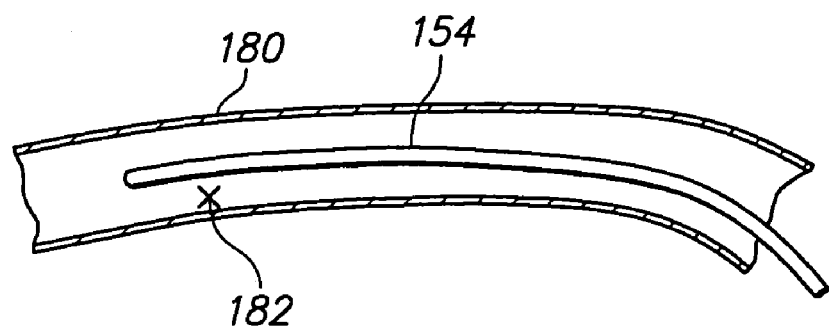
FIGS. 14A–14F are side views illustrating a method of intravascularly delivering the medical device of FIG. 1 into a blood vessel of a patient using the kit of FIG. 10.

Having described the structure of the intravascular lead kit 150, a preferred method of installing the medical device 100 within a patient's body in order to perform a therapeutic or diagnostic procedure will now be described, with reference to FIGS. 14A–14F. First, from a remote access site, such as the inner jugular vein or femoral vein (not shown), the guidewire 154 is routed into a selected blood vessel 180 until the distal end of the guidewire 154 extends past a target site 182 (FIG. 14A). To facilitate the correct routing and placement of the guidewire 154, diagnostic imaging, such as fluoroscopy, magnetic resonance imaging (MRI), and computer tomography (CT), is preferably used to track the distal end of the guidewire 154. As will be described in further detail below, the access site into the vasculature will ultimately depend on the selected implantation site of the stimulation and/or recording device. For example, if the stimulation/recording device is to be implanted within the chest or clavical region, or behind the ear, of the patient, the jugular vein should be selected as the access point. If, on the other hand, the stimulation/recording device is to be implanted within the abdominal or groin region of the patient, the femoral vein should be selected as the access point.

Figure 14B:
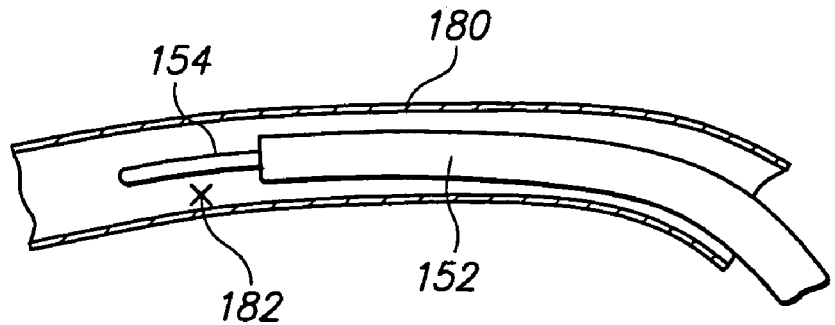
Figure 14C:
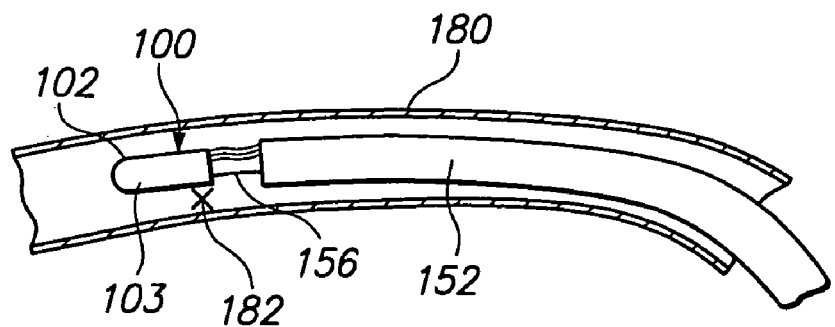
Figure 14D:
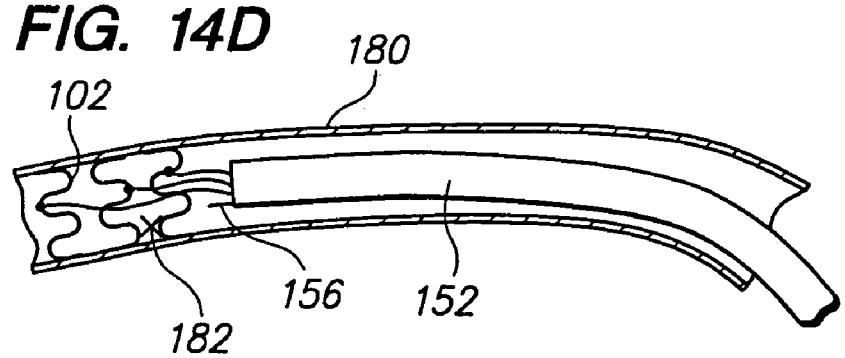
Figure 14E:
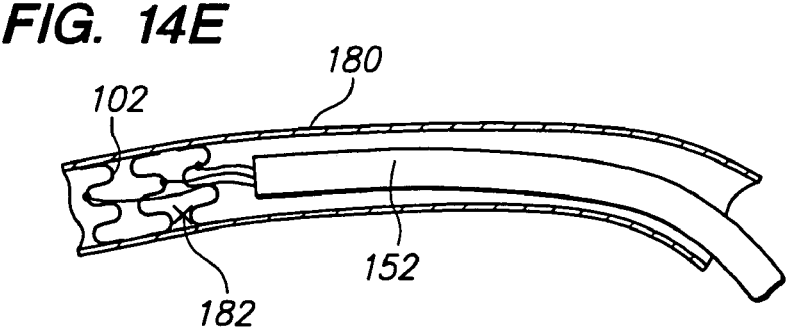
Figure 14F:
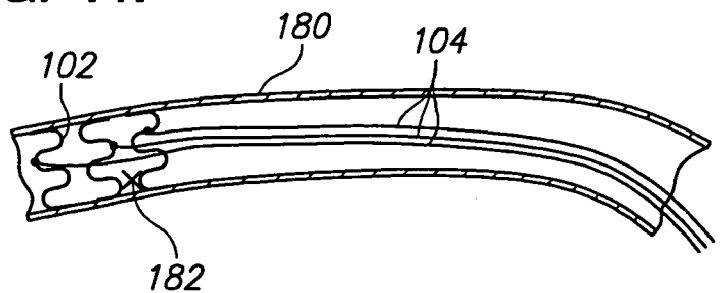

Next, the delivery catheter 152 is introduced over the guidewire 154 until the distal end of the catheter 152 is just proximal to the target site 182 (FIG. 14B). Once proper placement of the catheter 152 is achieved, the guidewire 154 is removed from the delivery lumen 166 via the proximal adapter 168 of the delivery catheter 152, and the medical device 100 and associated pusher element 156 are inserted into the delivery catheter 152 via the proximal adapter 168, and then distally advanced through the delivery catheter 152 until the collapsed electrode body 102 deploys out from the distal end of the catheter 152 adjacent the target site 182 (FIG. 14C). Alternatively, rather than using a separate guidewire and delivery catheter, the device 100 may resemble an "on a wire" type device (e.g., a guidewire or soft tip design is integrated into the device 100), in which case the device 100 is advanced to the target site 182 under its own influence. Next, the sheath 103 is removed from the electrode body 102, which then expands into firm contact with the inside of the blood vessel 180 (FIG. 14D). The pusher element 156 is then electrolytically detached from the electrode body 102 and removed from the delivery catheter 152 via the proximal adapter 168 (FIG. 14E). As previously discussed, detachment of the pusher element 156 can be accomplished by applying an electrical current to the proximal end of the core wire 158, which as previously described above, causes the sacrificial joint 162 (shown in FIG. 13) on the core wire 158 to dissolve in the presence of blood. If desired, additional medical devices 100 can be placed within the same or different blood vessel in a similar manner.

After the medical device 100 has been deployed within the patient, the delivery catheter 152 is removed from the patient's body. Depending on the nature of the disorder and goals of the operation, the medical device 100 may be left within the patient either acutely (i.e., only during an operation and then removed after the operation has been completed), chronically, or sub-chronically (i.e., less than six months). In any event, the proximal ends of the leads 104 of the medical device 100 will remain outside of the patient's body after the deployment process is completed, and in particular, will extend from the vascular access point, e.g., the internal jugular vein or femoral vein. The exposed ends of the leads 104 can be subcutaneously routed a short distance to the clavical or chest region or behind the ear of the patient (in this case where the jugular vein is the access point) or the abdominal or groin region of the patient (in the case where the femoral vein is the access point), where they can be coupled to the implanted stimulation/recording device. Alternatively, the stimulation/recording device 100 may not be implanted, but rather located exterior to the patient, e.g., during a non-chronic procedure.

Figure 15:
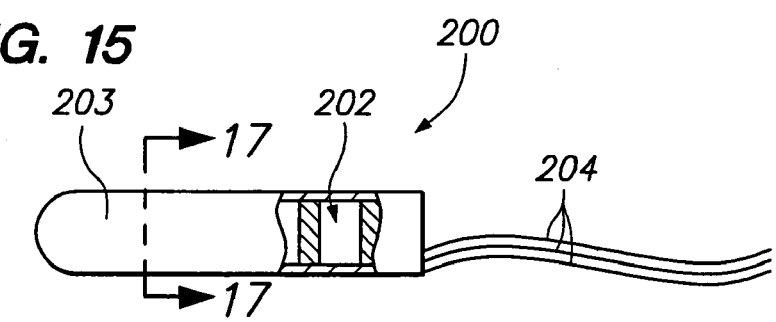
FIG. 15 is a partially cutaway side view of another intravascular medical device constructed in accordance with a preferred embodiment of the present inventions, wherein the medical device is particularly shown in a collapsed geometry.
Figure 16:
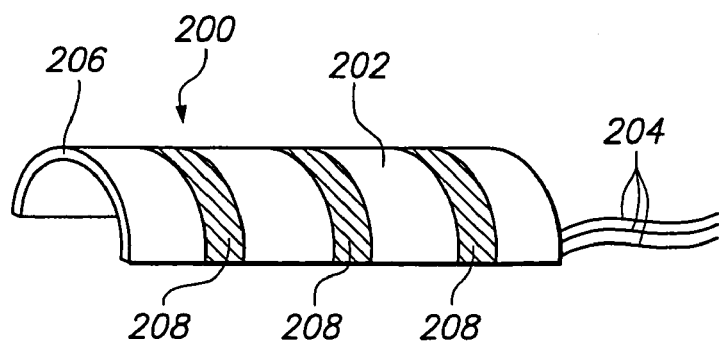
FIG. 16 is a perspective view of the medical device of FIG. 15, particularly shown in an expanded geometry.
Figure 17:
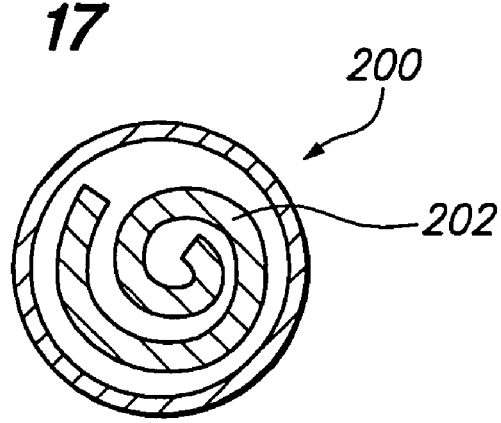
FIG. 17 is a cross-sectional view of the medical device of FIG. 1, taken along the line 17—17.

Referring now to FIGS. 15–17, an intravascular medical device 200 constructed in accordance with another preferred embodiment of the present inventions will be described. The medical device 200 comprises an expandable/collapsible electrode body 202, and a plurality of flexible conductive leads 204 electrically coupled to the electrode body 202. The electrode body 202 can be transformed from a collapsed geometry (FIGS. 15 and 17) into an expanded geometry (FIG. 16).

In its collapsed geometry, the electrode body 202 can be intravascularly delivered to a target site within a vessel using a standard stent delivery apparatus. In order to maintain the electrode body 202 in its collapsed geometry, a removable sheath or covering 203 is disposed over the collapsed electrode body 202, as shown in FIG. 15. The sheath 203 may have one or more delivery wires (not shown) that can be pulled in order to remove the sheath 203 from the electrode body 202, thereby allowing the electrode body 202 to be placed in its expanded geometry, as shown in FIG. 16. In its expanded geometry, the electrode body 202 can be placed into firm contact with the target site and used to transmit electrical signals to and/or receive electrical signals from the blood vessel and surrounding tissue, while minimizing blood occlusion.

The electrode body 202 comprises an arcuate resilient spring 206 and a plurality of electrodes 208 (in this case, three) disposed on the spring 206. The resilient spring 202 is non-tubular, i.e., its arcuate shape spans less than 360 degrees. In this manner, unlike tubular electrode structures, the electrode body 202 is more adaptable to variously sized blood vessels. In addition, the transmitted and/or recorded electrical energy is more focused. Preferably, the arcuate shape of the arcuate spring 206 spans greater than 180 degrees, so that it is capable of being frictionally adhered to the inner surface of a blood vessel.

The spring 206 is pre-shaped to assume its arcuate shape in the absence of an external force, but can be collapsed, e.g., by rolling the spring 206. Thus, the electrode body 202 can be placed and maintained in its collapsed geometry by applying a compressive force on the spring 206 and placing it within the sheath 203. In contrast, the electrode body 202 can be placed in its expanded geometry by releasing the compressive force to unfurl the spring 206, which naturally occurs when the sheath 203 is removed.

When expanded within a blood vessel, the resiliency of the spring 206 continuously urges it against the inner surface of the blood vessel with a force sufficient to hold the electrode body 202 in place within the selected blood vessel without moving as a result of the repetitive blood pulsing within the vascular system, but without distending the vessel wall. In the illustrated embodiment, the spring 206 is nonporous, but can alternatively be skeletal in nature, such as a coil, mesh, or braid. The surface of the arcuate spring 206 is preferably both biocompatible and electrically insulative. The arcuate spring 206 can be entirely composed of a resilient insulative material, such as polyimide, polytetrafluoroethylene (PTFE), Fluorinated Ethylene Propylene (FEP), polyethylene, or silicone, or can be composed of a core of electrically conductive material, such as one or more of the various materials from which the previously described conductive sub-structures 106 are composed, and an insulative layer disposed over the core.

In the illustrated embodiment, the electrodes 208 are applied to the spring 206 as a layer of highly electrically conductive and biocompatible material, such as gold, silver, or platinum. Deposition techniques include sputtering, vapor deposition, ion beam deposition, electroplating over a deposited seed layer, or a combination of these processes. Alternatively, the electrodes 208 may be discrete and flexible elements, such as mesh or braid, that is suitably bonded to the spring 206. In other alternative embodiments, the spring 206, itself, may form the electrodes 208. For example, any of the previously described techniques, such as forming electrodes from electrically conductive sub-structures, or removing insulative material to expose portions of an electrically conductive core, can be used.

The leads 204, the proximal ends of which will extend from the intravascular access point in the patient (e.g., the femoral vein or jugular vein), are configured to be coupled to an implanted or external source and/or recorder of the electrical signals (not shown), as will be described in further detail below. The conductive leads 204, which are of similar construction and length as leads 104, are suitably coupled to the electrodes 208 using means, such as welding or soldering.

Figure 18A:
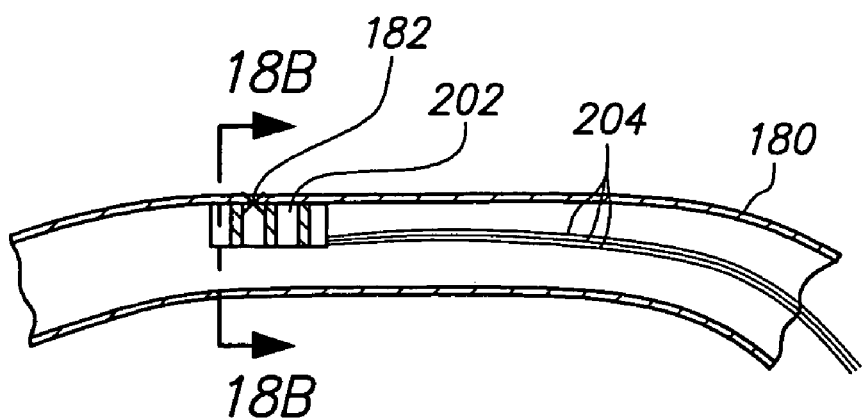
FIG. 18A is a side view of the medical device of FIG. 15 expanded within a blood vessel.
Figure 18B:
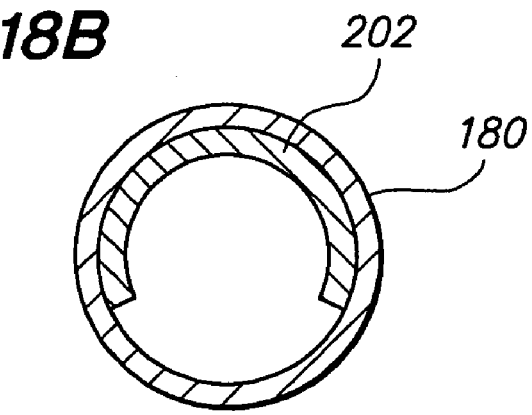
FIG. 18B is a cross-sectional view of the medical device and blood vessel of FIG. 18A taken along the line 18B—18B.

Using the delivery catheter 152, with the associated guidewire 154 and electrolytic pusher wire 156, the medical device 200 can be delivered to a target site 182 within a selected blood vessel in the same manner as that described above, so that the electrode body 202 is expanded into firm contact with the blood vessel 180, as illustrated in FIGS. 18A and 18B.

Figure 19:
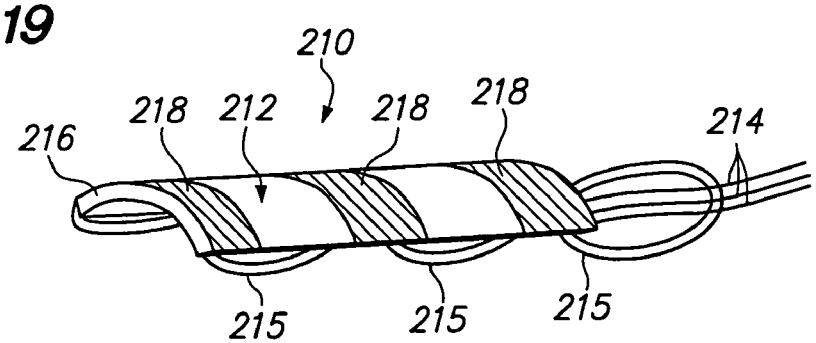
FIG. 19 is a perspective view of still another intravascular medical device constructed in accordance with a preferred embodiment of the present inventions, wherein the medical device is particularly shown in a collapsed geometry.
Figure 20:
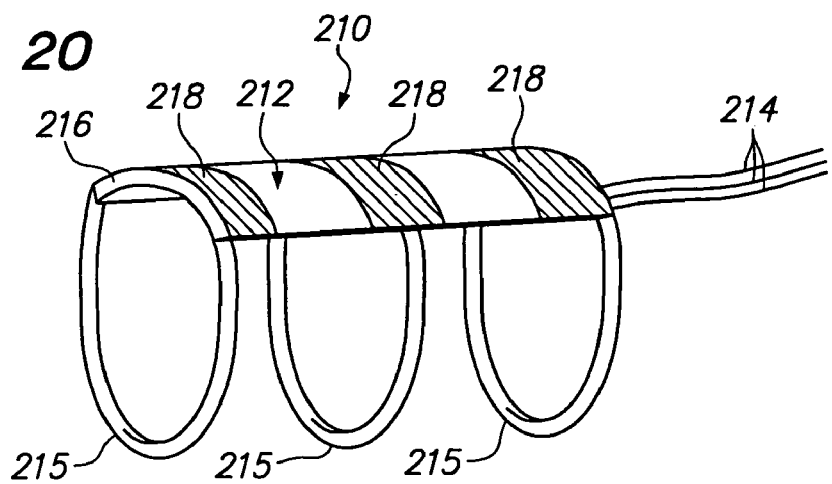
FIG. 20 is a perspective view of the medical device of FIG. 19, particularly shown in an expanded geometry.

Referring now to FIGS. 19 and 20, an intravascular medical device 210 constructed in accordance with still another preferred embodiment of the present inventions will be described. The medical device 210 comprises an expandable/collapsible electrode body 212 and a plurality of flexible conductive leads 214 electrically coupled to the electrode body 212. The electrode body 212 can be transformed from a collapsed geometry (FIG. 19) into an expanded geometry (FIG. 20). In its collapsed geometry, the electrode body 212 can be intravascularly delivered to a target site within a vessel using a standard stent delivery apparatus. In its expanded geometry, the electrode body 212 can be placed into firm contact with the target site and used to transmit electrical signals to and/or receive electrical signals from the blood vessel and surrounding tissue, while minimizing blood occlusion.

The electrode body 212 comprises an arcuate structure 216, a plurality of electrodes 218 (in this case, three) disposed on the structure 216, and a plurality of resilient spring loops 215 mounted to the arcuate structure 216. The spring loops 215 can be mounted to the arcuate structure 216 in any suitable manner, including welding or soldering. The spring loops 215 are pre-shaped to extend laterally from the arcuate structure 216 in the absence of a compressive force, but can be collapsed, e.g., by applying a compressive force to the spring loops 215. Thus, the electrode body 212 can be placed in its collapsed geometry by applying a compressive force to hinge the spring loops 215, which naturally occurs when the electrode body 212 is introduced within the delivery catheter 152. In contrast, the electrode body 212 can be placed in its expanded geometry by releasing the compressive force in order to hinge the spring loops 215 into their laterally extending position, which naturally occurs when the electrode body 212 exits the delivery catheter 152. The resiliency of the spring loops 215 continuously urges the arcuate structure 216 against the opposing vessel wall into firm contact with the target site with a force sufficient to hold the electrode body 212 in place within the selected blood vessel without moving as a result of the repetitive blood pulsing within the vascular system, but without distending the vessel wall.

Like the previously described arcuate spring 206, the arcuate structure 216 is non-tubular, i.e., its arcuate shape spans less than 360 degrees, thereby providing the electrode body 212 with the same advantages as the electrode body 202. Unlike the previously described electrode body 202, however, the electrode body 212 can advantageously span less than 180 degrees, since the electrode body 212 need not have the capability, by itself, to adhere to the vessel walls. That is, the force applied by the spring loops 215 is sufficient to place the electrode body 212 firmly against the vessel wall. In this manner, the electrode body 212 may be even more adaptable to a variety of blood vessel shapes, and the electrical stimulation and/or recording energy more focused, than that of the previously described arcuate electrode body 202.

Like the previously described arcuate spring 206, the surface of the arcuate structure 216 is preferably both biocompatible and electrically insulative, and thus can be constructed in a similar manner as the spring 206, with the exception that the arcuate structure 216 need not be resilient. Optionally, however, the arcuate structure 216 may be composed of a resilient material, so that it acts as a spring much like the resilient spring 206 of the electrode body 202. In this manner, the frictional engagement created by the resiliency of the spring, in addition to the lateral forces created by the resiliency of the spring loops 215, will place the electrodes 218 firmly in contact with the vessel wall.

The electrodes 218 can be composed of the same material and be disposed on the arcuate structure 216 in the same manner as the previously described electrodes 208. In addition to the electrodes 218, the resilient spring loops 215 can be composed of an electrically conductive material, so that they can also serve as electrodes. In this case, the spring loops 215 can be directly mounted to the electrodes 218. Alternatively, the spring loops 215 can act as electrodes, obviating the need for separate electrodes 218 on the arcuate structure 216.

The conductive leads 214, the proximal ends of which will extend from the intravascular access point in the patient (e.g., the femoral vein or jugular vein), are configured to be coupled to an implanted or external source and/or recorder of the electrical signals (not shown), as will be described in further detail below. The conductive leads 214, which are of similar construction and length as leads 104, are suitably coupled to the electrodes 218 using means, such as welding or soldering.

Figure 21A:
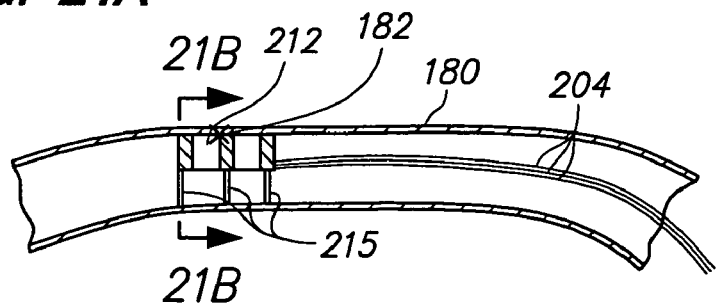
FIG. 21A is a side view of the medical device of FIG. 19 expanded within a blood vessel.
Figure 21B:
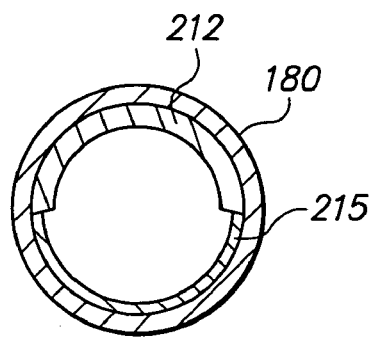
FIG. 21B is a cross-sectional view of the medical device and blood vessel of FIG. 21A taken along the line 21B—21B.

Using the delivery catheter 152, with the associated guidewire 154 and electrolytic pusher wire 156, the medical device 210 can be delivered to a target site 182 within a selected blood vessel in the same manner as that described above, so that the electrode body 212 is placed into firm contact with the blood vessel 180, as illustrated in FIGS. 21A and 21B.

Figure 22:
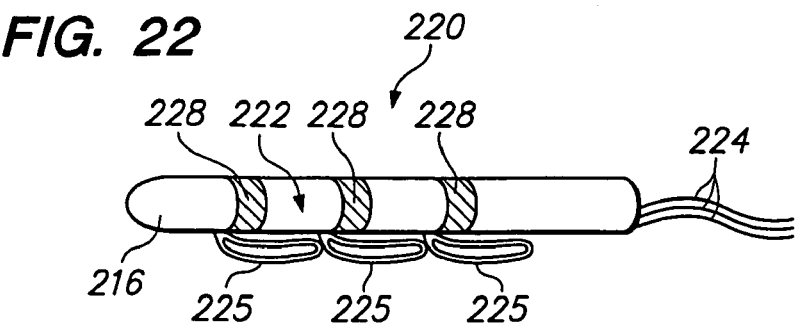
FIG. 22 is a perspective view of yet another intravascular medical device constructed in accordance with a preferred embodiment of the present inventions, wherein the medical device is particularly shown in a collapsed geometry.
Figure 23:
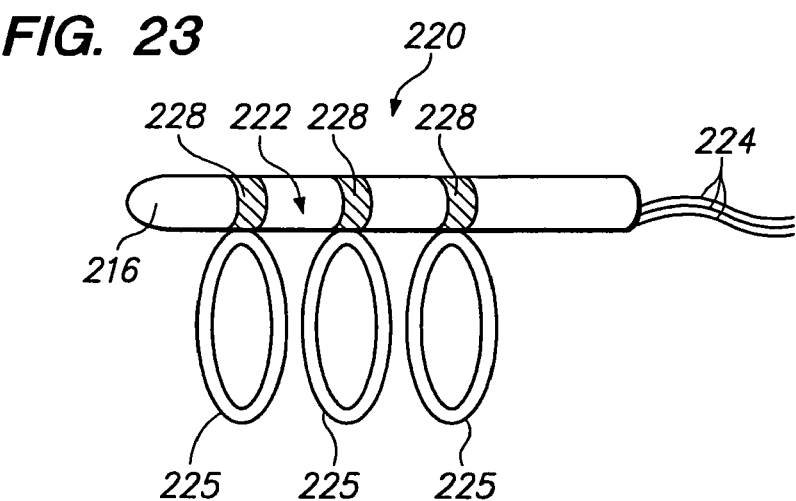
FIG. 23 is a perspective view of the medical device of FIG. 22, particularly shown in an expanded geometry.

Referring now to FIGS. 22 and 23, an intravascular medical device 220 constructed in accordance with yet another preferred embodiment of the present inventions will be described. The medical device 220 comprises an expandable/collapsible electrode body 222 and a plurality of flexible conductive leads 224 electrically coupled to the electrode body 222. The electrode body 222 can be transformed from a collapsed geometry (FIG. 22) into an expanded geometry (FIG. 23). In its collapsed geometry, the electrode body 222 can be intravascularly delivered to a target site within a vessel using a standard stent delivery apparatus. In its expanded geometry, the electrode body 222 can be placed into firm contact with the target site and used to transmit electrical signals to and/or receive electrical signals from the blood vessel and surrounding tissue, while minimizing blood occlusion.

The electrode body 222 comprises an elongated cylindrical member 226, a plurality of electrodes 228 (in this case, three) disposed on the cylindrical member 226, and a plurality of resilient spring loops 225 mounted to the cylindrical member 226. The spring loops 225 can be mounted to the cylindrical member 226 in any suitable manner, including welding, soldering, or tying the spring loops 225 to the cylindrical member 226. Like the previously described spring loops 225, the spring loops 225 are pre-shaped to extend laterally from the cylindrical member 226 in the absence of a compressive force, but can be collapsed, e.g., by applying a compressive force to the spring loops 225. The resiliency of the spring loops 225 continuously urges the cylindrical member 226 against the opposing vessel wall into firm contact with the target site with a force sufficient to hold the electrode body 222 in place within the selected blood vessel without moving as a result of the repetitive blood pulsing within the vascular system, but without distending the vessel wall.

The cylindrical member 226 can be composed of any flexible and insulative material, such as Pebax®, nylon, silicone, or urethane. In the illustrated embodiment, the electrodes 228 take the form of a ring electrodes that axially extend along the member 226. The electrodes 228 may be discrete elements that are mounted to the cylindrical member 226 in an interference relationship, or may be suitably formed on the cylindrical member 226 as a layer of material. The electrodes 228 may be composed of the same material as the previously described electrodes 208. Like the previously described spring loops 225, the resilient spring loops 225 can also be composed of an electrically conductive material in order to serve as electrodes, in which case, the spring loops 225 can be directly mounted to the electrodes 228, or alternatively, the spring loops 225 can act as electrodes, obviating the need for separate electrodes 228 on the cylindrical member 226.

The conductive leads 224, the proximal ends of which will extend from the intravascular access point in the patient (e.g., the femoral vein or jugular vein), are configured to be coupled to an implanted or external source and/or recorder of the electrical signals (not shown), as will be described in further detail below. The conductive leads 224, which are of similar construction and length as leads 104, extend through the cylindrical member 226 where they are suitably coupled to the electrodes 228 using means, such as welding or soldering.

Figure 24A:
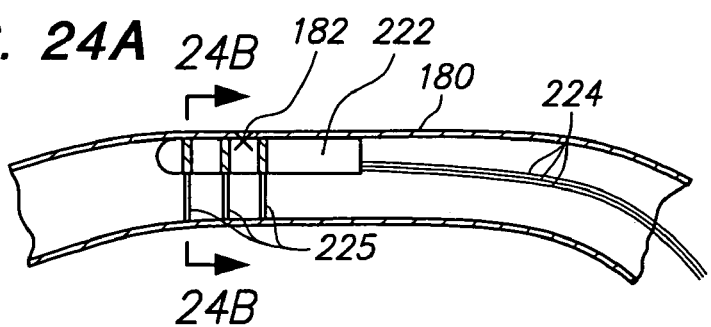
FIG. 24A is a side view of the medical device of FIG. 22 expanded within a blood vessel.
Figure 24B:
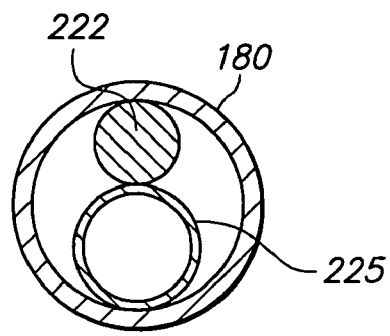
FIG. 24B is a cross-sectional view of the medical device and blood vessel of FIG. 24A taken along the line 24B—24B.

Using the delivery catheter 152, with the associated guidewire 154 and electrolytic pusher wire 156, the medical device 220 can be delivered to a target site 182 within a selected blood vessel in the same manner as that described above, so that the electrode body 222 is placed into firm contact with the blood vessel 180, as illustrated in FIGS. 24A and 24B.

Figure 25:
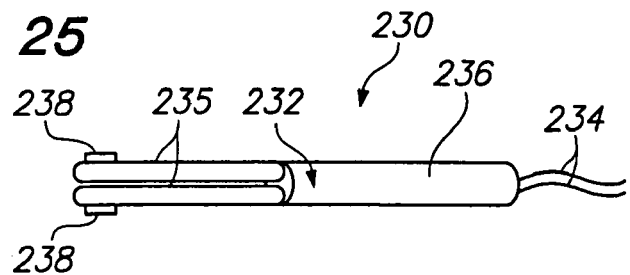
FIG. 25 is a perspective view of yet another intravascular medical device constructed in accordance with a preferred embodiment of the present inventions, wherein the medical device is particularly shown in a collapsed geometry.
Figure 26:
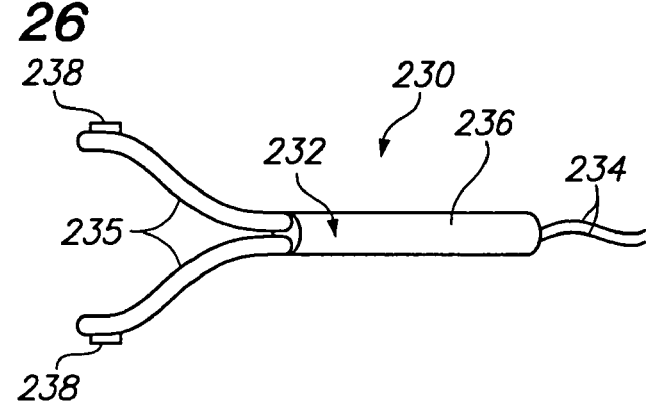
FIG. 26 is a perspective view of the medical device of FIG. 25, particularly shown in an expanded geometry.

Referring now to FIGS. 25 and 26, an intravascular medical device 230 constructed in accordance with yet another preferred embodiment of the present inventions will be described. The medical device 230 comprises an expandable/collapsible electrode body 232 and a plurality of flexible conductive leads 234 electrically coupled to the electrode body 232. The electrode body 232 can be transformed from a collapsed geometry (FIG. 25) into an expanded geometry (FIG. 26). In its collapsed geometry, the electrode body 232 can be intravascularly delivered to a target site within a vessel using a standard stent delivery apparatus. In its expanded geometry, the electrode body 232 can be placed into firm contact with the target site and used to transmit electrical signals to and/or receive electrical signals from the blood vessel and surrounding tissue, while minimizing blood occlusion.

The electrode body 232 comprises a central support member 236, a pair of resilient spring arms 235 extending from the distal end of the support member 234, and a pair of electrodes 238 disposed on the distal ends of the respective spring arms 235. The support member 236 can be composed of any suitable rigid or semi-rigid insulative material, such as Pebax®, nylon, urethane, silicone, or polyimide.

The spring arms 235 can be mounted to the support member 236 in any suitable manner, including welding or soldering. The spring arms 235 are pre-shaped to laterally extend away from each other in the absence of a compressive force to place the electrode body 232, but can be collapsed, e.g., by applying a compressive force to the spring arms 235. Thus, the electrode body 232 can be placed and maintained in its collapsed geometry by applying a compressive force to move the spring arms 235 towards each other, which naturally occurs when the electrode body 232 is introduced within the delivery catheter 152. A sheath (not shown) can be optionally used to maintain the electrode body 232 in its collapsed geometry as it is introduced through the delivery catheter 152. In contrast, the electrode body 232 can be placed in its expanded geometry by releasing the compressive force to allow the spring arms 235 to move away from each other, which naturally occurs when the electrode body 232 exits the delivery catheter 152. When the spring arms 235 expand against the vessel wall, they will create an anchoring force sufficient to hold the electrode body 232 in place within the selected blood vessel without moving as a result of the repetitive blood pulsing within the vascular system, but without distending the vessel wall.

In the illustrated embodiment, the electrodes 238 are discrete elements that are suitably bonded onto the resilient arms 235, although the electrodes 238 can be formed onto the spring arms 235 in other suitable manners. With the exception of their distal ends, the spring arms 235 are preferably coated with an electrically insulative material. Alternatively, the exposed distal ends of the spring arms 235 can act as electrodes, thereby obviating the need to bond separate discrete electrodes 238 onto the spring arms 235.

The conductive leads 234, the proximal ends of which will extend from the intravascular access point in the patient (e.g., the femoral vein or jugular vein), are configured to be coupled to an implanted or external source and/or recorder of the electrical signals (not shown), as will be described in further detail below. The conductive leads 234, which are of similar construction and length as leads 104, extend through the support member 236 and are suitably coupled to the proximal ends of the spring arms 235 using means, such as welding or soldering.

Figure 27A:
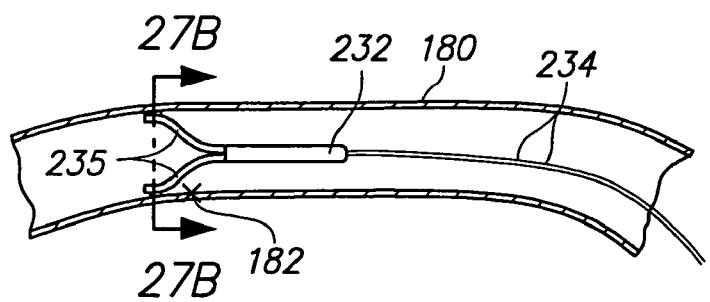
FIG. 27A is a side view of the medical device of FIG. 25 expanded within a blood vessel.
Figure 27B:
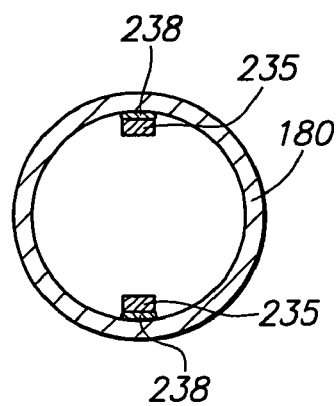
FIG. 27B is a cross-sectional view of the medical device and blood vessel of FIG. 27A taken along the line 271B—27B.

Using the delivery catheter 152, with the associated guidewire 154 and electrolytic pusher wire 156, the medical device 230 can be delivered to a target site 182 within a selected blood vessel in the same manner as that described above, so that the electrode body 232 is placed into firm contact with the blood vessel 180, as illustrated in FIGS. 27A and 27B.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An expandable intravascular medical device, comprising:
   an electrode support structure;
   at least one electrode associated with the support structure;
   a plurality of resilient spring loops laterally extending from the support structure, wherein the entirety of each of the spring loops is disposed on one side of the support structure; and
   at least one lead electrically coupled to the at least one electrode.

2. The medical device of claim 1, wherein the support structure is a non-tubular arcuate structure.

3. The medical device of claim 1, wherein the support structure is a cylindrical member.

4. The medical device of claim 1, wherein the support structure forms the at least one electrode.

5. The medical device of claim 1, wherein at least one electrode is formed by at least one of the spring loops.

6. The medical device of claim 1, wherein the at least one electrode comprises a plurality of electrodes, and the at least one lead comprises a plurality of leads electrically coupled to the respective electrodes.

7. A method of performing a medical procedure on a patient, comprising:
   intravascularly introducing the medical device of claim 1 into the patient while the medical device is in a collapsed geometry;
   placing the medical device in an expanded geometry to firmly contact the at least one electrode with the inner surface of the blood vessel; and
   transmitting and/or receiving electrical signals between the blood vessel and the at least one electrode.

8. The method of claim 7, wherein the medical device is placed in the collapsed geometry by applying a compressive force to the spring loops, and placed in the expanded geometry by releasing the compressive force from the spring loops.

9. The method of claim 7, further comprising implanting the medical device within the blood vessel.

10. A method of performing a medical procedure on a patient using a medical device, the medical device including two resilient spring arms extending distally from an elongated member, an electrode associated with the distal end of one of the spring arms, and a lead electrically coupled to the electrode, the method comprising:
    intravascularly introducing the medical device into a blood vessel of the patient while the spring arms are laterally moved towards each other to place the medical device is in a collapsed geometry;
    laterally moving the spring arms away from each other into contact with an inner surface of the blood vessel to place the medical device in an expanded geometry to firmly contact the electrode with the inner surface of the blood vessel and anchor the medical device within the blood vessel; and
    transmitting and/or receiving electrical signals between the blood vessel and the electrode.

11. The medical device of claim 10, wherein the medical device is placed in the collapsed geometry by applying a compressive force to the spring arms, and placed in the expanded geometry by releasing the compressive force from the spring arms.

12. The medical device of claim 10, further comprising implanting the medical device within the blood vessel.

13. The method of claim 10, wherein the medical device further includes another electrode associated with the distal end of the other of the spring arms.

14. The method of claim 13, wherein the device further includes another lead electrically coupled to the other electrode.

15. The method of claim 10, wherein the distal end of the one spring arm forms the electrode.

16. The method of claim 10, wherein the spring arms are pre-shaped to laterally move away from each other.

17. An expandable intravascular medical device, comprising: a non-tubular arcuate spring; at least one electrode associated with the arcuate spring; and at least one lead electrically coupled to the at least one electrode.

18. The medical device of claim 17, wherein the arcuate spring spans greater than 180 degrees.

19. The medical device of claim 17, wherein the arcuate spring forms the at least one electrode.

20. The medical device of claim 17, wherein the at least one electrode comprises a plurality of electrodes, and the at least one lead comprises a plurality of leads electrically coupled to the respective electrodes.

21. A method of performing a medical procedure on a patient, comprising:
intravascularly introducing the medical device of claim 17 into the patient while the medical device is in a collapsed geometry; placing the medical device in an expanded geometry to firmly contact the at least one electrode with the inner surface of the blood vessel; and transmitting and/or receiving electrical signals between the blood vessel and the at least one electrode.

22. The method of claim 21, wherein the medical device is placed in the collapsed geometry by applying a compressive force to the arcuate spring, and placed in the expanded geometry by releasing the compressive force from the arcuate spring.

23. The method of claim 21, further comprising implanting the medical device within the blood vessel.

24. The medical device of claim 17, wherein the arcuate structure has an inner electrically insulative surface.

25. An expandable intravascular medical device, comprising: a non-tubular arcuate structure having an inner electrically insulative surface and an outer electrically insulative surface; at least one electrode disposed on the outer electrically insulative surface of the arcuate structure; and at least one lead electrically coupled to the at least one electrode.

26. The medical device of claim 25, wherein at least a portion of the arcuate structure forms the at least one electrode.

27. The medical device of claim 25, wherein the arcuate structure is non-porous.

28. The medical device of claim 25, wherein the at least one electrode comprises an electrically conductive film.

29. The medical device of claim 25, wherein the at least on electrode comprises a plurality of electrodes, and the at least one lead comprises a plurality of leads electrically coupled to the respective electrodes.

30. An expandable intravascular medical device, comprising: a non-tubular, resilient, arcuate structure having an inner electrically insulative surface; at least one electrode associated with the arcuate structure; and at least one lead electrically coupled to the at least one electrode.

31. An expandable intravascular medical device, comprising: a non-tubular arcuate structure having an inner electrically insulative surface; at least on electrode associated with the arcuate structure; at least one lead electrically coupled to the at least one electrode; and a resilient support structure disposed on the outside of the arcuate structure.

32. A method of performing a medical procedure on a patient using a medical device comprising a non-tubular arcuate structure having an inner electrically insulative surface, and at least one electrode associated with the arcuate structure, the method comprising: intravascularly introducing the medical device into a blood vessel of the patient while the medical device is in a collapsed geometry; placing the medical device in an expanded geometry to firmly contact the at least one electrode with the inner surface of the blood vessel; and transmitting and/or receiving electrical signals between the blood vessel and the at least one electrode.

33. The method of claim 32, wherein the medical device is in a collapsed geometry by applying a compressive force to the arcuate structure, and placed in the expanded geometry by releasing the compressive force from the arcuate structure.

34. The method of claim 32, further comprising implanting the medical device within the blood vessel.

* * * * *